(12) United States Patent
Jury

(10) Patent No.: US 7,263,886 B2
(45) Date of Patent: Sep. 4, 2007

(54) APPARATUS FOR AND METHODS OF STRESS TESTING METAL COMPONENTS

(76) Inventor: Brent Felix Jury, 158 Mahostahi RD42, Waitara, New Plymouth (NZ)

( * ) Notice: Subject to any disclaimer, the term of this patent is extended or adjusted under 35 U.S.C. 154(b) by 104 days.

(21) Appl. No.: 10/527,908

(22) PCT Filed: Sep. 22, 2003

(86) PCT No.: PCT/NZ03/00216

§ 371 (c)(1),
(2), (4) Date: Mar. 14, 2005

(87) PCT Pub. No.: WO2004/026659

PCT Pub. Date: Apr. 1, 2004

(65) Prior Publication Data

US 2006/0059992 A1    Mar. 23, 2006

(30) Foreign Application Priority Data

Sep. 20, 2002   (NZ) ...................................... 521541

(51) Int. Cl.
*G01N 29/11* (2006.01)
(52) U.S. Cl. ............................ 73/579; 73/1.86; 73/599; 73/602
(58) Field of Classification Search ................... 73/579, 73/597, 598, 599, 600, 602, 1.86, 582, 583, 73/778
See application file for complete search history.

(56) References Cited

U.S. PATENT DOCUMENTS

| | | | |
|---|---|---|---|
| 3,347,335 A | 10/1967 | Watters | |
| 4,893,511 A | 1/1990 | Voigt et al. | |
| 5,127,333 A | 7/1992 | Theurer | |
| 5,265,831 A * | 11/1993 | Muller | ........................ 246/124 |
| 5,520,052 A | 5/1996 | Pechersky | |

(Continued)

FOREIGN PATENT DOCUMENTS

GB   2372569 A   8/2002

(Continued)

*Primary Examiner*—Hezron Williams
*Assistant Examiner*—Jacques M. Saint-Surin
(74) *Attorney, Agent, or Firm*—O. (Sam) Zaghmout; Bio Intellectual Property Services (Bio IPS) LLC

(57) ABSTRACT

A tuning device (23) and an apparatus that incorporates the tuning device (23) for use in testing the integrity of a railway line (30) to obtain an improved test signal, the tuning device (23) including an elongate member (23) adapted to be attachable at one end of the railway line (30) being tested in situ or is attachable to an attachment member (21) coupled to the section (10) of railway line (30), and wherein a vibration signal measuring means (24) is adapted to be secured to the other end of the elongate member (23). The apparatus can include a control means (2), a vibration means (3), the tuning device (23) configured and arranged to be attachable to the railway line (30) and a vibration measuring means (24) is attachable to the railway line (3) to directly vibrate the section (10) of the railway line (30), the control means (2) controlling the frequency of vibration and to receive and process measurements of the amplitude of vibration from the tuning device (23) and the frequency of vibration from the vibration measuring means (24).

16 Claims, 3 Drawing Sheets

U.S. PATENT DOCUMENTS

| | | | |
|---|---|---|---|
| 5,627,425 A | 5/1997 | Kaida et al. | |
| 5,698,788 A * | 12/1997 | Mol et al. | 73/659 |
| 6,026,687 A * | 2/2000 | Jury | 73/582 |
| 6,031,790 A * | 2/2000 | Futsuhara et al. | 367/96 |
| 6,116,088 A * | 9/2000 | Schneider et al. | 73/579 |
| 6,216,985 B1 * | 4/2001 | Stephens | 246/120 |
| 6,655,639 B2 * | 12/2003 | Grappone | 246/120 |
| 6,951,132 B2 * | 10/2005 | Davenport et al. | 73/598 |

FOREIGN PATENT DOCUMENTS

| | | |
|---|---|---|
| GB | 2383413 A | 6/2003 |
| JP | 2001333023 A | 11/2001 |
| SU | 1606985 A | 11/1990 |
| WO | WO97/04291 A | 2/1997 |

* cited by examiner

APPARATUS FOR AND METHODS OF STRESS TESTING METAL COMPONENTS

TECHNICAL FIELD

This invention relates to improvements in and relating to devices and apparatus for testing metal components, and methods and systems associated therewith. More particularly, but not exclusively, this invention relates to methods of testing the integrity of railway lines.

BACKGROUND ART

Metal components suffer from a degree of residual stress caused by actions such as mechanical or thermal loading. The presence of stress affects the physical properties of a metal component and can result in stress fatigue and even failure of a component.

Methods available for measuring residual stress in metal components are not in widespread usage. Current practice is generally simply to subject a metal component to thermal stress relieving techniques regardless of the actual need. Therefore a significant wastage of resources arises in heat treating metal components not requiring stress relief.

A related problem arises with elongate components such as railway lines and pipelines. A railway track is generally laid in such a way as to be under a neutral load condition at a predetermined temperature. When the track is above the neutral temperature the railway line as a whole is placed under compression as the sections expand. At excessive levels this can result in the track buckling. At temperatures lower than the neutral temperature the track lengths exist in tension. At some point if the tensile forces are high enough, ie the temperature is low enough, the sections of track can snap.

Because of the outcome of the snapping of sections of track is not as much of a safety hazard as buckling of track the neutral temperature is typically set above the average summertime temperature. In New Zealand the neutral temperature is set at around 30 degrees Celsius.

Railway lines undergo considerable thermal cycling. They are also subjected to significant mechanical loading as trains ride over the rails. This can result in plastic deformation of the rails, that is, the rails stretch. When that happens the neutral temperature of the rails drops, and thus the risk of track buckling on hot days increases. It is generally accepted that railway lines need to be reset or restretched. More particularly, they need to be re-laid under tension in order to reset the neutral temperature every ten years or so to minimise the risk of buckling. At present it is a costly and time consuming exercise to uplift a railway line to restretch and relay it. Significant resources can be wasted on restretching sections of track that do not require any stretching.

It is an object of the invention to provide a device and/or an apparatus for use in testing the integrity of metal components and sections of railway line that overcomes at least some of the abovementioned problems, or at least to provide the public with a useful choice.

SUMMARY OF THE INVENTION

According to a broad aspect of the invention there is provided a tuning device for use in testing the integrity of a railway line to obtain an improved test signal, the tuning device including an elongate member adapted to be attachable at one end to the railway line being tested in situ or is attachable to an attachment member coupled to the section of railway line, and wherein a vibration signal measuring means is adapted to be secured to the other end of the elongate member.

Preferably the vibration signal measuring means is a transducer means. Desirably the transducer means is an accelerometer.

Preferably the elongate member is made of a suitable metal. Desirably the tuning device is made of a non-brittle, high tensile, material that has a sufficient amount of elasticity and ductility.

Advantageously the elongate member is fastened to an attachment member, and wherein the attachment member is releasably clamped to the head of a railway line. Desirably the attachment member is an L shaped block of metal that is mild steel.

Preferably a dampening means is secured to the elongate member adjacent the vibration signal measuring means to allow for the tuning frequency of the tuning device to be set. Desirably the dampening means is tubular and is provided with a hollow central section, and wherein a dampening material is provided within the hollowed central section.

Preferably in one application of the testing apparatus the elongate member is substantially about 13.5 centimeters between an attachment point on the railway line or attachment member and the vibration signal measuring means, and the elongate member is substantially about 16 millimeters in width and about 3 millimetees in thickness, and wherein the tuning device is tuned to measure frequencies at about 80 Hertz.

According to a second aspect of the invention there is provided an apparatus for testing the integrity of a section of railway line including a control means, a vibration means, a tuning device configured and arranged to be attachable to said section of railway line in accordance with the first aspect of the invention, and a vibration measuring means, the vibration means being associated with a said section of railway line, in use, to directly vibrate the section of railway line, the control means controlling the frequency of vibration and to receive and process measurements of the amplitude of vibration from the tuning device and the frequency of vibration from the vibration measuring means.

Preferably the apparatus further includes a temperature measurement means attachable to the said section of railway line to provide a temperature signal to the control means.

Desirably the vibration means is a motor having eccentric weights mounted about the motor shaft, and wherein the vibration measurement means is a tachometer mounted to the shaft of the motor.

Advantageously the distance between the tuning device and the vibration means is any suitable distance to achieve accurate test measurements and is desirably between substantially about 60 to 70 centimeters but it will be appreciated that variants of these measurements are possible within the scope of the invention.

According to a third aspect of the invention there is provided a system of testing the integrity of a section of railway line, the system including the apparatus of the second aspect of the invention associated with a section of railway line running over five consecutive railway sleepers aligned transversely under the railway line, the vibration means, in use, being coupled to the railway line adjacent the second sleeper and an accelerometer or the tuning device according to any one of claims 1 to 10 being attachable to the section of railway line adjacent the fourth sleeper, and wherein the distance between the vibration means and the accelerometer or the tuning device is between about 60 to 75 centimeters.

Preferably the system is configured and arranged wherein the second, third and fourth sleepers are unclipped from the railway line and packing members are placed between the top of the second and fourth sleepers and the underside of the railway line respectively to form an air gap between the third sleeper and the underside of the railway line.

BRIEF DESCRIPTION OF THE DRAWINGS

Preferred embodiments of the invention will now be illustrated, by way of example only, with reference to the accompanying drawings in which.

DETAILED DESCRIPTION OF THE DRAWINGS

Figure 1:
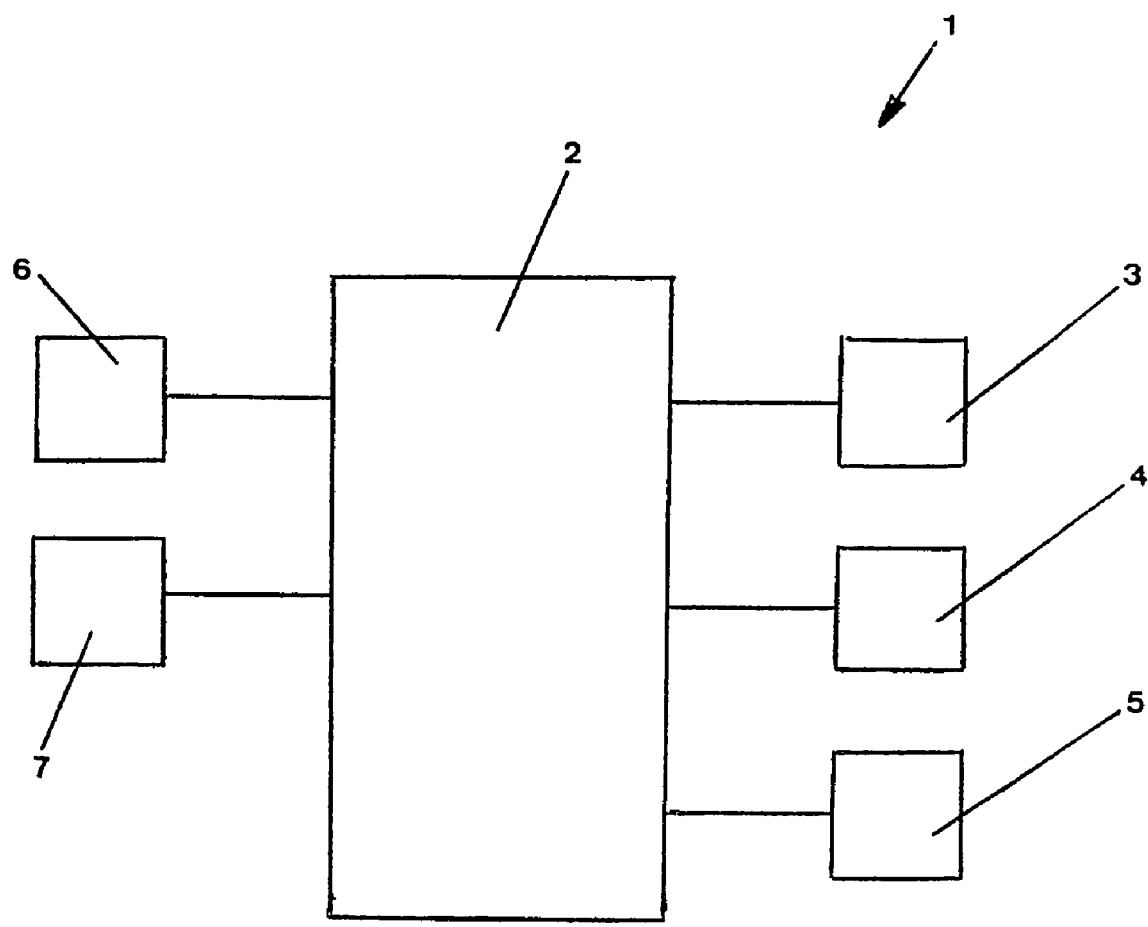
FIG. 1: illustrates a block diagram of general components of the apparatus of the invention.

Referring to FIG. 1, a block diagram of general components of the apparatus of the invention, generally referred to as 1, is illustrated.

The apparatus 1 can be provided to test the integrity of a metal component. The metal component can desirably be of any suitable type for testing purposes by vibration. It will be appreciated that references herein to a railway line can also be references to other metal components, including pipelines. However, for simplicity of description of the invention the embodiments thereof will refer herein to railway lines.

Further, this invention is related to the invention as described in WO 97/04291 and U.S. patent specification No. 6,026,687 and the full description of the patentee's invention as described in those documents is incorporated herein as part of this description. A person skilled in the art would have ready access to those documents and the description contained therein when seeking to appreciate and understand aspects of the present invention.

The apparatus 1 preferably includes a control means 2 in the form of a computer means having a microprocessor programmed to control the operation of the apparatus 1 and including the steps of obtaining measurements and data from the various measuring instruments, processing the inputted signals into a desirable form suitable for storage and/or display purposes. With respect to storage purposes the data may be manipulated to provide statistical data showing characteristics of the railway line or section of railway line 10 being tested.

The control means 2 can function to control each step of the method of the invention. The control means 2 can desirably be powered by any suitable and durable battery means (not shown) for remote testing on say railway track away from an electrical power source and to allow the apparatus to have portable applications rather than merely laboratory workbench applications.

A vibration means 3 can be mounted by any known and suitable securing means, such as for example a clamp, to an appropriate area of the railway line. Desirably the vibration means is in the form of a motor adapted with a vibration inducement means preferably in the form of eccentric weights mounted to the motor shaft that apply a vibration force on the line. Such force is adjustable such that the frequency of vibration can be changed as required. The vibration means 3 may include an exciter or shaker, as it is known in the art, that is desirably controlled by a user controlling and adjusting the speed of the motor 3. The motor 3 can be controlled by being associated with the control means 2.

The motor speed of the vibration means can be sensed using any known form of motor speed measuring means and in this embodiment is in the form of a tachometer 4 that can be mounted to the shaft of the motor 3. The tachometer 4 measures the shaft speed and the measured signal outputs are fed to the control means 2.

The amplitude of vibration induced on a section of railway line is sensed and measured using a signal measuring means in the form of a transducer means, desirably an accelerometer 5. It will be appreciated that any suitable known instrument may be used or applied.

The accelerometer 5 generates an electrical signal in response to the vibration acceleration of the railway line as induced by the vibration means 3, and provides a signal that is fed to the control means 2. The control means 2 is configured and arranged to convert the signals into a measurement of frequency of vibration.

A temperature measurement means 6 with a suitably sensitive sensing means can measure the temperature of the line during measurements. The temperature measurements means 6 is desirably in the form of a pyrometer and provides a measurement to the control means 2 that allows the temperature of the line to be tagged against other recorded data at the time of testing.

A display means 7 can be provided to display the plotted measurements of velocity amplitude (for example, in mm/second) against the frequency of vibration and any other desirable characteristics of the data obtained in the testing phase of the operation.

Figure 2:
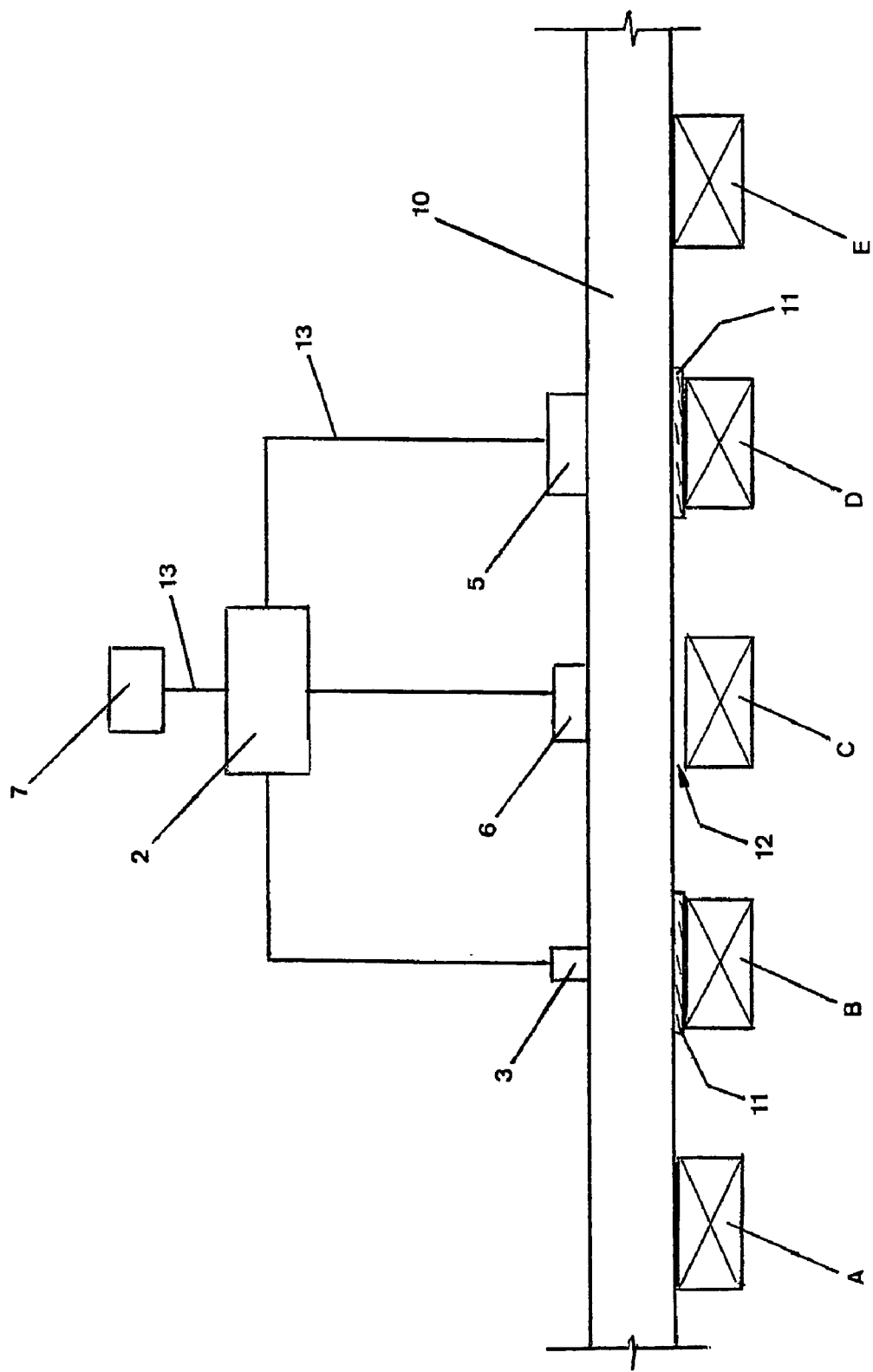
FIG. 2: illustrates the system of attachment of the apparatus of FIG. 1 to a section of railway line.

Referring now to FIG. 2, a system of attachment of the apparatus 1 to a section of railway line before testing of the said section of railway line, is illustrated.

Persons skilled in the art will appreciate that railway lines undergo constant compression or tension caused by changes to temperature about the line and other factors. Rapid changes in temperature or unacceptably high or low temperatures can induce undesirable levels of stress that can cause railway lines to buckle.

Some railway lines are joined in sections. Adjoining sections of line must be laid at a similar level of tension or compression, and can be desirably laid at a neutral state at a certain temperature. If adjoining sections are in a substantially different state and temperature fluctuations are rapid, buckling or other undesirable movements in the line can occur. The invention can assist with testing the integrity of railway lines to determine whether relaying or replacement of sections of line is required, and may provide an aid to the proper laying or relaying of railway lines.

In one non-limiting method and system of testing, a section of railway line 10 for testing is seen in FIG. 2 as resting on five railway sleepers, defined as first sleeper A, second sleeper B, third sleeper C, fourth sleeper D, and fifth sleeper E. These five sleepers can be unclipped from the line to be tested or may be left clipped in position during testing, as required. The first sleeper A and the fifth sleeper E can be preferably rigidly secured and having ballast compacted and in contact with the sides of the first sleeper A and the fifth sleeper E such that the underside of the sleepers A and E can be in contact with the ballast. It will be appreciated by one skilled in the art that ballast can also be used on other sleepers as required to ensure proper contact during testing.

The second sleeper B, the third sleeper C and the fourth sleeper D can be unclipped from the line 10. A packing member 11 in the form of a shim or the like is placed between the top of the second sleeper B and the underside of the line 10. A shim 11 can also be placed between the top of the fourth sleeper D and the underside of the railway line 10. A gap is advantageously left between the top of the third sleeper C and the underside of the railway line 10, generally indicated by 12.

The arrangement of the second, third and fourth sleepers relative to the line 10 can be considered important for one form of testing in accordance with the system of testing using the apparatus 1.

The accelerometer 5 can be mounted to the line 10 desirably above the fourth sleeper D. Advantageously the accelerometer 5 is mounted in a tuning arrangement as described below with reference to FIGS. 3 and 4. The vibration means 3 can be coupled or mounted above the second sleeper B. The temperature measurement means 6 can be mounted in any suitable position on the line 10. All necessary data lines are connected to the control means 2 by hard wire 13 or otherwise, such as, for example, infra red or laser signal. Any known methods of data communications may be employed as required.

In one operation, a method of testing the integrity of the line 10 is described. The vibration means 3 is activated and the accelerometer 5 provides a feedback signal to the control means 2. The signal can be processed to a digital form and a display means 7 displays a plot of the velocity amplitude of vibration (mm/sec) against the frequency of vibration (hertz). The frequency of vibration can be increased, generally in most applications testing can be achieved in the operating frequency range of between 0 to 100 hz in some situations but may be increased to any suitable frequency up to substantially 500 Hz or thereabouts as required. A reasonably linear measurement of amplitude of vibration is measurable by the accelerometer 5 that can also be displayed. The vibration may be increased until a noticeable spike is detected.

With some railway lines a spike or loading node may be detected at between 50 hz and 125 hz. If the line is in tension the spike may be detected between 50 hz and 75 hz. If the line is in compression a noticeable spike is detectable at between about 85 hz and 100 hz. This information is useful for determining whether a section of railway line requires re-stretching or replacement and provide an indication of the condition of the line 10.

It will be appreciated that in one alternative embodiment, the accelerometer 5 may be placed between the sleeper C and sleeper D and the vibration means 3 mounted above the second sleeper B to allow desirable and accurate measurements to be obtained in accordance with the invention. The accelerometer 5 and the vibration means 3 should preferably be mounted at least 60 cm apart.

Figure 3:
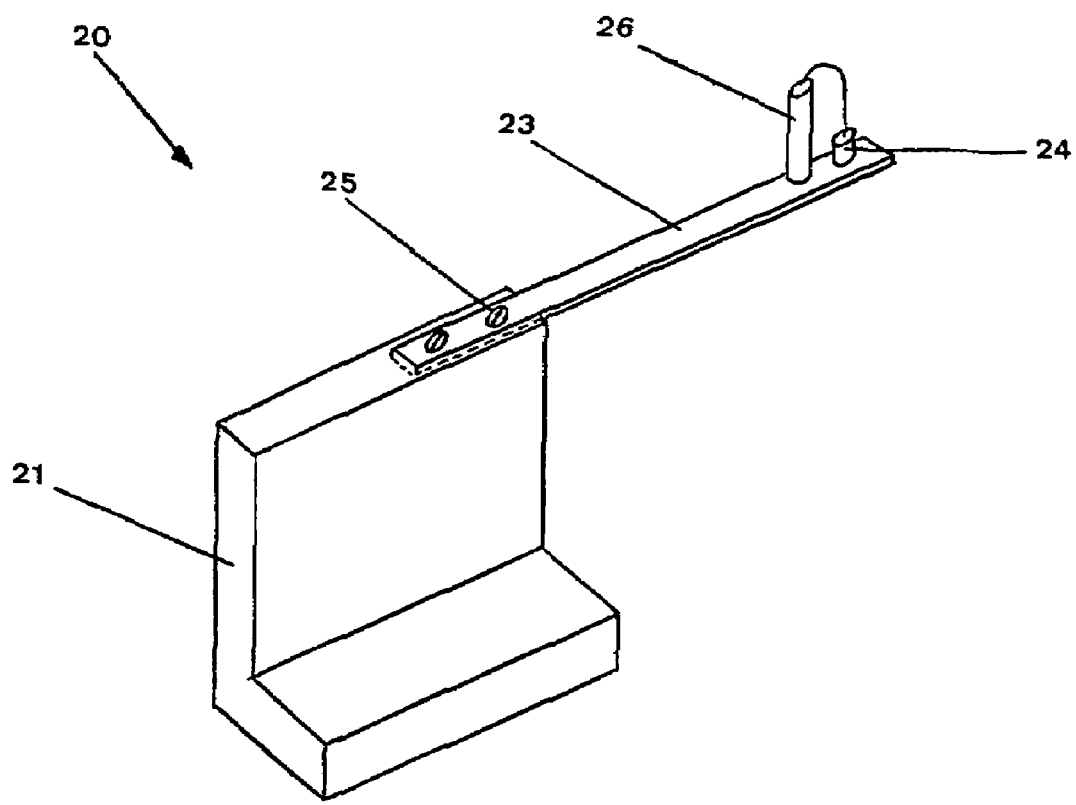
FIG. 3: illustrates the tuning device and an arrangement on an attachment member.
Figure 4:
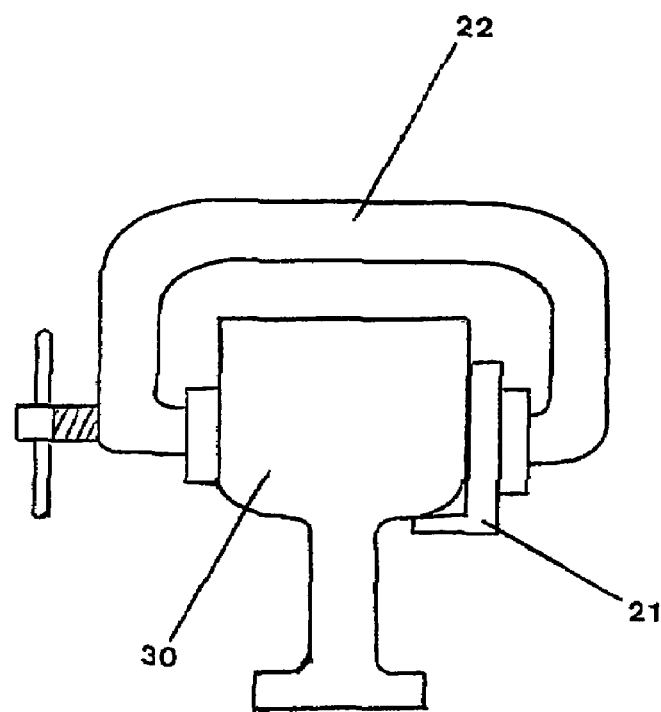
FIG. 4: illustrates one form of attachment of the tuning device to a section of railway line.

Referring now to FIGS. 3 and 4, a tuning arrangement for obtaining an electrical signal representing the frequency of vibration on a railway line, generally referred to as 20, is illustrated.

The tuning arrangement 20 is designed to improve the quality of the signal by reducing errors caused by the standard clamping system incorporated with attaching or coupling an accelerometer directly to the railway line.

A tuning device may desirably include an attachment member in the form of a base member 21 that functions to anchor or couple the signal measuring means or transducer means to the railway line 30. The base member 21 may be preferably in the form of an L-cross section and is large enough to allow any suitable and durable clamping means 22 to clamp the tuning arrangement to the line 30. As seen clearly in FIG. 4, desirably the base member 21 is clamped to the outside of the line 30 as it is considered to be an area of the line that does not wear to the same extent as the inside head section of a standard two rail line.

A tuning device 23 is made of any suitable and durable material, and functions to couple the transducer means in the form of an accelerometer 24 base member 21 via the elongate member 23 and allow accurate measurements to be taken. A non-brittle elastic material can be suitably used, and a high tensile mild steel metal is desirable, as it is tough and ductile. A light metal with a high elasticity can be advantageous.

The near end of the elongate member 23 can be located in a slot (not shown) in an edge of the base member 21 for increased coupling and attached to the base member 21 by any suitable attachment means. In this example screws 25 are shown. The accelerometer 24 can be secured to the elongate member 23 at the distal end. A dampening means 26 may be included adjacent the accelerometer 24 at the distal end of the elongate member 23.

The dampening means 26 may desirably be in the form of a tubular dampener 26 having a hollow section allowing a material to be added within to set the desired tuning frequency of the tuning arrangement. Desirably sand is used in the dampener. In one desirable embodiment the dampener 26 can possibly be about 15 millimeters ("mm") in height and about 3 millimeters in diameter. Other dimensions and shapes are envisaged within the scope of the invention.

In one non-limiting example, the elongate member 23 can be about 13.5 cm between the screw 25 and the accelerometer 24 and be about 16 mm in width and about 3 mm in thickness. These dimensions may be provided when the tuning device is being used to measure frequencies at about 78 hz or 80 hz.

It may well be that a more sensitive tuning device 23 can be provided when the thickness of the device 23 is reduced.

It will be appreciated that when the base member 21 is clamped to the line the tuning device 23 is in parallel with the railway line. It is considered to be desirable to have the tuning device 23 in parallel with the railway line for increased accuracy.

In yet a further embodiment or set up arrangement for testing as an alternative to the previous methods as described with reference to FIG. 2, no shims or packing need be used, and the railway line 30 can remain clipped to the sleepers.

In this method with unclipped railway lines, the vibration means 3 is located over sleeper B, and the base member 21 is clamped, and more preferably can be T-clamped, to the line between sleeper C and sleeper D, and desirably halfway between sleeper C and sleeper D. The coupled tuning device 23 and accelerometer 24 may be positioned at about at least 60 cm from the vibration means 3 and more preferably substantially about 70 cm from the tuning device 23 to obtain more accurate results and to avoid or minimlise interference from the vibration means 3.

Advantageously, the feedback signal from the accelerometer 5 to the control means 2 can be provided to the control means 2 via an infra red or laser signal means. The receiver for the infra red or laser signal may be attached to a rail car that is movable on the line, and wherein the testing and measuring apparatus of the invention is located.

It is considered that one desirable tuned frequency is 80 hz as it is considered a suitable frequency for testing resulting in reasonable amplification of the velocity amplitude signals sensed by the accelerometer 24. This is bearing in mind that the resonant frequencies of many railway lines are well above this frequency.

The invention further includes suitable computer software for controlling the operation of the computer or computer means that forms part of the control unit 2. Preferably the computer processing steps for controlling the operation of the apparatus for testing the integrity of a railway line includes the steps of obtaining data on the frequency of vibration of the line by using a suitable measuring device such as a tachometer. It will be appreciated that close control of the vibration means is possible using the tachometer to sense motor speed and to provide a signal to the control unit 2. The control unit 2 may then provide a signal to adjust motor speed as appropriate.

The accelerometer 5 provides a signal of the amplitude of vibration of the line. The temperature measurement means 6 desirably provides a signal of the temperature of the line.

Once this data has been obtained, the next step is executed in that a graph can be plotted showing the amplitude of vibration against the frequency of vibration at a determined temperature of the line. The resultant data is then recorded and can be later compared against other derived data as required.

Preferably the computer processing steps further include the step of comparing the plots for a section of line being tested at different line temperatures and determining whether the line is in compression or tension.

Desirably the processing steps included the preliminary step of obtaining a reference measurement of the velocity amplitude of the line when in a neutral position defined as being neither in compression or tension. This measurement can be recorded for comparison purposes for all plots at different line temperatures.

Wherein the aforegoing reference has been made to integers or components having known equivalents, then such equivalents are herein incorporated as if individually set forth. Accordingly, it will be appreciated that changes may be made to the above described embodiments of the invention without departing from the principles taught herein.

Additional advantages of the present invention will become apparent for those skilled in the art after considering the principles in particular form as discussed and illustrated. Thus, it will be understood that the invention is not limited to the particular embodiments described or illustrated, but is intended to cover all alterations or modifications which are within the scope of the appended claims.

The invention claimed is:

1. A tuning device for use in testing the integrity of a railway line to obtain a vibration test signal, the tuning device including an elongate member adapted to be attachable at one end to the railway line being tested in situ or is attachable to an attachment member coupled to the section of a said railway line so as to allow, in use, the other end of the elongate member to extend freely therefrom, the elongate member being made of a non-brittle and elastic material suitable for enabling a vibration signal measuring means to be securable to the elongate member, in use, so as to measure the vibration signals on the said railway line.

2. A tuning device in accordance with claim 1 wherein the vibration signal measuring means is a transducer means.

3. A tuning device in accordance with claim 2 wherein the transducer means is an accelerometer.

4. A tuning device in accordance with claim 1 wherein the elongate member is made of mild steel.

5. A tuning device in accordance with claim 1 wherein the elongated member is made of a non-brittle, high tensile, material that has sufficient elasticity and ductility.

6. A tuning device according to claim 1 wherein the one end of the elongate member is fastenable to an attachment member, and wherein the attachment member is a block of metal, in use, that is releasably clampable to the head of a railway line.

7. A tuning device according to claim 1 wherein the attachment member is an L shaped block of metal adapted to be releasably clampable to the head of a railway line.

8. A tuning device according to claim 1 wherein a dampening means is secured to the elongate member adjacent the vibration signal measuring means to allow for the tuning frequency of the tuning device to be set.

9. A tuning device according to claim 1 wherein the dampening means is tubular and is provided with a hollow central section, and wherein a dampening material is provided within the hollowed central section.

10. A tuning device according to claim 1 wherein the elongate member is substantially about 13.5 centimeters between an attachment point on the railway line or attachment member and the vibration signal measuring means, and the elongate member is substantially about 16 millimeters in width and about 3 millimeters in thickness, and wherein the tuning device is tuned to measure frequencies at about 80 Hertz.

11. An apparatus for testing the integrity of a section of railway line, the apparatus including a control means, a vibration means, a tuning device including an elongate member adapted to be attachable at one end to the railway line being tested in situ or is attachable to an attachment member that is in turn coupled to the section of a said railway line so as to allow, in use, the other end to extend freely therefrom, the elongate member being made of a non-brittle and elastic material suitable for enabling a vibration signal measuring means to be secured to the elongate member, in use, so as to measure vibration signals on the said railway line and the vibration signal measuring means, the vibration means being associated with a said section of railway line, in use, to directly vibrate the section of railway line, the control means controlling the frequency of vibration and to receive and process measurements of the amplitude of vibration from the vibration signal measuring means of the tuning device and the frequency of vibration from the vibration means.

12. An apparatus according to claim 11 further including a temperature measurement means attachable to the said section of railway line to provide a temperature signal to the control means.

13. An apparatus according to claim 11 wherein the vibration means is a motor having eccentric weights mounted about the motor shaft, and wherein the vibration measurement means is a tachometer mounted to the shaft of the motor.

14. An apparatus according to either claim 11 or claim 12 wherein the distance between the tuning device and the vibration means is between about 60 to 70 centimeters.

15. A system of testing the integrity of a section of railway line, the system including an apparatus having a control means, a vibration means, and a tuning device, the tuning device comprising an elongate member adapted to be attachable at one end to the railway line being tested in situ or is attachable to an attachment member that is in turn coupled to the section of a said railway line so as to allow, in use, the other end to extend freely therefrom and being substantially in parallel to the said railway line, the elongate member being made of a non-brittle and elastic material suitable for enabling a vibration signal measuring means to be secured to the elongate member, in use, so as to measure vibration signals on the said railway line, and the vibration signal measuring means, the vibration means being associated with a said section of railway line, in use, to directly vibrate the section of railway line, the control means controlling the frequency of vibration and to receive and process measurements of the amplitude of vibration from the vibration signal measuring means of the tuning device and the frequency of vibration from the vibration means, the apparatus being set up on a section of railway line running over five consecutive railway sleepers aligned transversely under the railway line, the vibration means, in use, being coupled to the railway line adjacent the second sleeper and an accelerometer or the tuning device being attachable to the section of railway line adjacent the fourth sleeper, and wherein the distance between the vibration means and the accelerometer or the tuning device is between about 60 to 75 centimeters.

16. A system according to claim 15 wherein the second, third and fourth sleepers are unclipped from the railway line and packing members are placed between the top of the second and fourth sleepers and the underside of the railway line respectively to form an air gap between the third sleeper and the underside of the railway line.

\* \* \* \* \*